United States Patent [19]

Wittwer

[11] Patent Number: 4,857,320

[45] Date of Patent: Aug. 15, 1989

[54] METHOD OF ENHANCING THE SOLUBILITY OF TISSUE PLASMINOGEN ACTIVATOR

[75] Inventor: Arthur J. Wittwer, Ellisville, Mo.

[73] Assignee: Monsanto Company, St. Louis, Mo.

[21] Appl. No.: 16,295

[22] Filed: Feb. 19, 1987

[51] Int. Cl.[4] ............................................. A61K 37/547
[52] U.S. Cl. ............................... 424/94.63; 424/94.64; 514/565
[58] Field of Search ...................... 514/565; 424/94.63, 424/94.64, 101

[56] References Cited

U.S. PATENT DOCUMENTS

| | | | |
|---|---|---|---|
| 2,521,793 | 9/1950 | Howe et al. | 167/58 |
| 3,920,838 | 11/1975 | Flatt et al. | 424/319 |
| 3,950,513 | 4/1976 | Jensen | 424/94 |
| 3,950,529 | 4/1976 | Fischer et al. | 424/273 |
| 4,285,964 | 8/1981 | Niebes et al. | 424/283 |
| 4,381,346 | 4/1983 | Husain | 435/215 |
| 4,409,233 | 10/1983 | Tsukada et al. | 424/273 R |
| 4,442,213 | 4/1984 | Heber et al. | 435/217 |
| 4,505,893 | 3/1985 | Mori et al. | 424/94 |
| 4,568,544 | 2/1986 | Hasegawa et al. | 424/94 |

FOREIGN PATENT DOCUMENTS 0041766 12/1981 European Pat. Off. .
217379 4/1987 European Pat. Off. .

OTHER PUBLICATIONS

Weimer et al., The Lancet, Nov. 7, 1981, pp. 1018–1020.
Collen et al., Thromb. Haemostas. 48, 294–296 (1982).
Camiolo et al., Prep. Biochem. 12(4), 297–305 (1982).
Husain et al., Proc. Natl. Acad. Sci. USA 78(7), 4265–9 (1981).
Smith et al., Biochem. J. 239, 477–479 (1986).
Binder et al, J. Biol. Chem., vol. 254, No. 6, 1979, pp. 1998–2003.

*Primary Examiner*—Johnnie R. Brown
*Assistant Examiner*—Jacqueline M. Stone
*Attorney, Agent, or Firm*—Scott J. Meyer; James W. Williams, Jr.

[57] ABSTRACT

The solubility of tissue plasminogen activator in aqueous solution is enhanced by incorporating therein arginine or a non-toxic salt of arginine in an amount effective to increase the solubility of the t-PA without substantially inhibiting its potential biological activity upon administration.

1 Claim, 1 Drawing Sheet

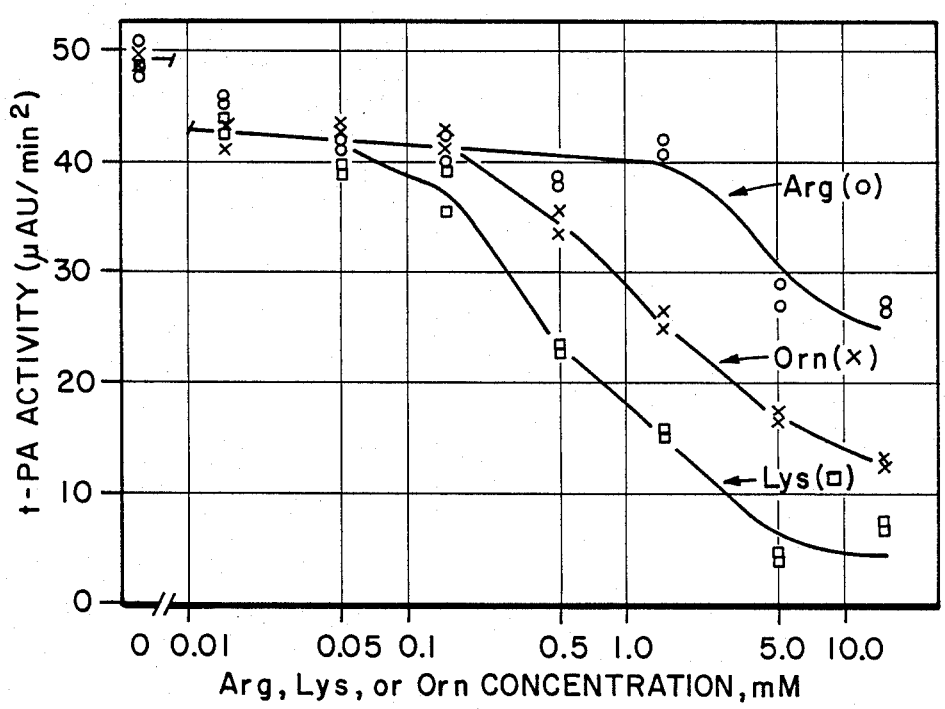

METHOD OF ENHANCING THE SOLUBILITY OF TISSUE PLASMINOGEN ACTIVATOR

BACKGROUND OF THE INVENTION

This invention relates to a tissue plasminogen activator solution and method of preparation. More particularly, the invention concerns the enhancement of the solubility of tissue plasminogen activator in aqueous media without thereby causing a substantial loss in its potential biological activity upon administration.

Tissue plasminogen activator (t-PA) is a proteinaceous material, preferably glycosylated, which has thrombolytic activity whereby it is therapeutically useful for the treatment of patients suffering from a thrombosis or blood clot. The t-PA is generally administered parenterally, such as intravenously, in the form of an aqueous solution of the drug. The solution needs to be physiologically acceptable so that in addition to delivery of the desired therapeutic component to the patient the solution does not otherwise adversely affect the patient's electrolyte and volume balance. The aqueous medium for the t-PA thus usually comprises normal physiologic saline (0.85% NaCl, 0.15M), pH 7-7.4.

One problem with t-PA, in general, is that it is not as readily soluble in aqueous media as optimally desired for certain indications such that a sufficient concentration of the drug can be administered rapidly to a patient in a reasonable volume of solution. For example, in order to provide t-PA in a potency sufficient for maximal efficacy, an excessive amount of saline solution may be required to dissolve the desired amount of t-PA with a result that upon administration it produces a disturbance in the patient's fluid volume or osmolality. Therefore, it would be desirable to enhance the solubility of t-PA so that the amount of administered solution containing the t-PA can be reduced.

Various attempts have been made heretofor to improve the solubility of t-PA in aqueous solution. Thus, pharmaceutically acceptable surface active agents such as the polyoxyethylene sorbitan monoesters, e.g. Tween® 80 (polysorbate 80), have been used for this purpose. Use of Tween 80 and elevation of the ionic concentration of the t-PA solution to 0.3M NaCl (hypertonic saline) has been used heretofor as disclosed by Weimar et al., *The Lancet.*, Nov. 7, 1981, pp. 1018-1020, and Collen et al., *Thrombo. Haemostas.* 48, 294-296 (1982). So also, lysine, ornithine and salts thereof have been reported as useful for increasing the solubility of t-PA in aqueous solution as seen from U.S. Pat. No. 4,568,544.

BRIEF DESCRIPTION OF THE INVENTION

In accordance with the present invention, an improved aqueous solution of t-PA is provided by incorporating in the solution arginine or a non-toxic salt of arginine in an amount effective to enhance the solubility of the t-PA. It has been found surprisingly that the arginine in the t-PA solution is substantially less inhibitory of the potential biological activity of t-PA upon administration than either lysine or ornithine, both of which have basic side chains similar to arginine. Since arginine also has been found herein to be somewhat better than lysine or ornithine in improving t-PA solubility in aqueous media, arginine has a distinct advantage over these other amino acids in therapeutic formulations of the drug.

Arginine has been widely used heretofore in parenteral solutions in combination with other amino acids for nutritional purposes or to restore nitrogen losses. See, for example, U.S. Pat. Nos. 2,521,793; 3,920,838; and 3,950,529. It has also been used to improve solubility of certain drugs in aqueous solution such as DOPA as described in U.S. Pat. No. 4,409,233 or catechin as disclosed in U.S. Pat. No. 4,285,964. Arginine has been used in elution solutions with phosphate buffered saline and other substances such as Tween 80 or EDTA for the gel filtration purification of t-PA as described in U.S. Pat. No. 4,505,893, or the fibrin-Celite® affinity chromatographic purification of t-PA as disclosed in U.S. Pat. No. 4,381,346, or in t-PA tissue extraction solutions of phosphate-detergent extractants containing 75 mM acetate, 0.3M NaCl, 10 mM EDTA and 0.25% Triton®X-100, pH 4.2, as reported by Camiolo et al., *Prep. Biochem.* 12(4), 297-305 (1982). However, arginine has not been known to be useful in therapeutic aqueous solutions of t-PA. The finding of the distinct advantage of arginine in promoting solubility of t-PA without substantially inhibiting the activity of t-PA was unexpected and unpredictable in view of the substantial loss of such activity observed with the closely related lysine and ornithine amino acids at similar concentrations in aqueous solution.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the accompanying drawings in which:

The FIGURE is a graphical representation which shows the influence of arginine as compared to lysine and ornithine on activity of t-PA (5 ng/ml) in aqueous solution in the parabolic rate assay. The data in this FIGURE are plotted in a semi-logarithmic configuration in which the t-PA activity in microabsorbance units per minute$^2$ ($\mu$AU/min$^2$) at 410 nm absorbance is shown in an arithmetic scale on the ordinate and the millimolar (mM) amino acid concentration is shown in a logarithmic scale on the abscissa.

As is well-known, t-PA can be obtained from various human and mammalian tissue sources and, in particular, can be isolated from culture fluids of normal human cells grown under in vitro cell culture conditions. Typical of these cells are kidney, lung, foreskin, skin and small intestines as described, for example, in U.S. Pat. Nos. 4,335,215; 4,505,893; 4,537,860; and 4,550,080.

Another suitable source of t-PA is the established human melamoma cell line (Bowes). See, for example, European Patent Application No. 41,766, published Dec. 16, 1981; Rijken and Collen, *J. Biol. Chem.* 256 (13), 7035-7041 (1981); and Kluft et al., *Adv. Biotech. Proc.* 2, Alan R. Liss, Inc., 1983, pp. 97-110. The Bowes melanoma t-PA is a glycoprotein which has a moleuclar weight of about 68,000-70,000 daltons and a 527 amino acid structure with serine as the N-terminal. The melanoma t-PA exists either as a single chain or as two chains, known as an A-chain and a B-chain. It also separates into two variants in the A-chain, known as types I and II, which differ by about $M_r$ 2000-3000. See Ranby et al., *FEBS Lett.* 146 (2), 289-292 (1982); Wallen et al., *Eur. J. Biochem.* 132, 681-686 (1983); Einarsson et al., *Biochim. Biophys. Acta* 830, 1–10 (1985); and Rijken et al., *Thromb. Haemostas.* 54(4), 788–791 (1985). Type I is glycosylated at Asn-117, Asn-184 and Asn-448 whereas Type II is glycolsylated only at Asn-117 and Asn-448 according to Pohl et al., *Biochemistry* 23, 3701–3707 (1984). A high mannose structure has been assigned to Asn-117 whereas complex carbohydrate structures are assigned to Asn-184 and Asn-448 by Pohl et al., "EMBO Workshop on Plasminogen Activators," Amalfi, Italy, Oct. 14–18, 1985.

Genetic information from the Bowes malanoma cell line also has been embodied in *E. coli* by conventional recombinant DNA gene splicing methods to permit the production of the t-PA protein moiety by that microorganism. See, for example, UK Patent Application No. 2,119,804, published Nov. 23, 1983; Pennica et al., *Nature* 301, 214–221 (1983); and Vehar et al., *Biotech.* 2 (12), 1051–1057 (1984). Recombinant t-PA produced by the expression of Bowes melanoma genetic material in cultured mammalian cells has been administered to humans with some measure of effectiveness. See Collen et al., *Circulation* 70 (16), 1012–1017 (1984).

Still another human source of t-PA is human uterine tissue as disclosed by Rijkin and Collen, *J. Biol. Chem.* 256(13), 7035–7041 (1981), and Pohl et al., *FEBS Lett.* 168(1), 29–32 (1984).

Production of glycosylated t-PA in non-human mammalian cells also is known. Thus, Kaufman et al., *Mol. Cell. Biol.* 5, 1750–1759 (1985), and European Patent Application No. 117,059, published Aug. 29, 1984, describe the use of Chinese hamster ovary cells and Browne et al., *Gene* 33, 279–284 (1985), describe the use of mouse L cells for such production.

Production of glycosylated t-PA by recombinant DNA yeast cells also has been reported. Thus, European Patent Application No. 143,081, published May 29, 1985, describes a recombinant yeast plasmid vector which encodes human t-PA from Hela cells. European Patent Application No. 174,835, published Mar. 19, 1986, describes a t-PA with selected glycosylation expressed in yeast. The cDNA encoding for the t-PA is derived from Bowes melanoma. European Patent Application No. 178,105, published Apr. 16, 1986, discloses a glycosylated uterine t-PA expressed in yeast cells or mouse cells. In the latter case, a bovine papilloma virus is used as the vector.

Still other variations of genetically engineered t-PA products are described in European Patent Applications Nos. 196,920, published Oct. 8, 1986; 199,574, published Oct. 19, 1986; and 201,153, published Nov. 12, 1986.

It will be appreciated that any of the foregoing or similar such sources of t-PA can be used in accordance with the present invention, although a preferred source is a glycosylated t-PA derived from cultured normal human colon cells as described in co-pending application Ser. No. 929,950, filed Nov. 12, 1986, now U.S. Pat No. 4,751,084 and assigned to the common assignee. The disclosure of said patent application is incorporated herein by reference.

The amount of arginine used to improve the solubility of t-PA without substantially inhibiting the desired biological activity of the t-PA in accordance with this invention can vary widely but preferably ranges from about one millimolar (1 mM) to about one molar (1M). Thus, 1 mM would contain about 174 mg arginine per liter of solution whereas 1M would contain about 174 g arginine per liter. Higher concentrations can be used but they do not appear to be necessary for the desired solubilization of the t-PA without inhibiting the t-PA activity as defined herein.

The arginine can be directly incorporated in the foregoing amounts in the final solution to be administered to the patient, or can be included in more concentrated forms, even in lyophilized form, for ultimate dilution in the final solution prior to administration.

The preferred non-toxic salt forms of arginine are acid salts such as the hydrogen halide salts, for example, HCl.

The amount of t-PA in the aqueous solution in combination with arginine or a non-toxic salt thereof is primarily dependent upon the physical characteristics of the recipient to which the therapeutic solution is to be administered and the severity of the thrombolytic condition. The amount to be administered must be an effective amount, that is, an amount which is medically beneficial but does not present toxic effects which overweigh the advantages which accompany its use. Amounts of t-PA ranging from about 0.05 to about 50 mg/ml in aqueous solution are generally suitable. This is equivalvent to a range of from about 25,000 to about $2.5 \times 10^7$ international units (IU) per ml.

The following examples will further illustrate the invention in greater detail although it will be appreciated that the invention is not limited to these specific examples.

In the parabolic rate assay employed herein, plasminogen activation was measured by hydrolysis of the chromogenic substrate S-2251 (H-D-Val-Leu-Lys-p-nitroanilide, KabiVitrum, Stockholm, Sweden), in an aqueous reaction mixture containing 0–10 ng/ml t-PA, 50 µg/ml plasminogen, 1 mM S-2251 and 130 µg/ml fragments of human fibrinogen (t-PA stimulator, KabiVitrum) in phosphate buffered saline, pH 7.4, containing 0.01% Tween 80 and 0.01% $NaN_3$. Under conditions of the assay, a linear production of plasmin with time is observed, resulting in hydrolysis of S-2251 and an increase of 410 nm absorbance which is parabolic in nature, or linear with the square of the reaction time. Activities were expressed in International Units (IU) relative to the WHO t-PA standard, lot 83/517, or in microabsorbance units at 410 nm per $\text{minute}^2$ ($\mu\text{AU/min}^2$). A t-PA concentration of 5 ng/ml in the assay was equivalent to about 2.5 IU/ml of the WHO standard and gave a response of about 50 $\mu\text{AU/min}.^2$. The general procedure for the parabolic rate assay is well-known and is described by Ranby, *Biochim. Biophys. Acta* 704, 461–469 (1982), and Verheijen et al., *Thromb. Haemostas.* 48, 266–269 (1982). In this assay, the t-PA stimulator mimics the stimulatory effects of fibrin. See Zamarron et al., *J. Biol. Chem.* 259, 2080–2083 (1984).

The single-chain and two-chain melanoma t-PA samples used herein were obtained commercially from American Diagnostica, Inc., Greenwich, Conn. (ADI).

EXAMPLE 1

This example shows the solubility and recovery of t-PA under varying conditions both with and without arginine-HCl additive in buffered aqueous solution. Thus, similar amounts of single-chain (ADI, Product 111, Lot 0776274) or two-chain (ADI, Product 110, Lot 0766232) melanoma t-PA (400,000 to 500,000 IU/mg, 50,000 to 60,000 IU total) were dissolved in 2 ml of PBSAT [phosphate buffered saline (Sigma, St. Louis, Mo., Product No. 1000-3) containing 0.01% $NaN_3$ and 0.01% Tween 80], pH 7.4, and dialyzed overnight (about 15–18 hours) against 250 volumes of the buffers specified in Table I, below. After dialysis, the samples were concentrated 14- to 29-fold by ultrafiltration using Amicon Centricon®-10 microconcentrators (10,000 mol. wt. cutoff with a YM10, low protein binding, membrane). Sample activity before and after concentration was measured in the parabolic rate assay and recovery of t-PA was calculated. Table I, below, sets forth the results of these tests. The results show that both single-chain and two-chain t-PA are provided with enhanced solubility by the incorporation of arginine in the aqueous solution of t-PA. The enhancement is substantially greater than that obtained by increasing the ionic strength of the solution such as by raising the NaCl concentration to 1M.

TABLE I

| t-PA and buffer | Before concentration Activity (IU/ml) | Volume (ml) | After concentration Activity (IU/ml) | Volume (ml) | Recovery (%) |
| --- | --- | --- | --- | --- | --- |
| Single-chain t-PA: | | | | | |
| PBSAT | 19,500 | 1.50 | 8,900 | 0.066 | 2 |
| PBSAT, 15 mM Arg—HCl | 28,000 | 1.85 | 40,100 | 0.119 | 9 |
| PBSAT, 150 mM Arg—HCl | 38,800 | 1.65 | 406,000 | 0.091 | 58 |
| PBSAT, 0.88 M NaCl (1 M NaCl total) | 37,500 | 1.60 | 90,600 | 0.056 | 8 |
| Two-chain t-PA: | | | | | |
| PBSAT | 22,900 | 1.80 | 26,000 | 0.079 | 5 |
| PBSAT, 15 mM Arg—HCl | 27,100 | 1.80 | 115,000 | 0.075 | 18 |
| PBSAT, 150 mM Arg—HCl | 31,500 | 1.65 | 499,000 | 0.063 | 60 |
| PBSAT, 0.88 M NaCl (1 M NaCl total) | 32,400 | 1.60 | 130,000 | 0.114 | 29 |

EXAMPLE 2

This example further demonstrates the solubility and recovery of t-PA under varying conditions both with and without arginine-HCl additive in aqueous solution. Identical amounts of two-chain melanoma t-PA (ADI, Product 110, Lot 52-03, about 500,000 IU/mg, 110 μg total) in a volume of 100 μl of 1M $NH_4HCO_3$, were added to the upper chamber of Amicon Centricon-10 microconcentrators. To each microconcentrator was then added 2 ml of various buffers indicated in Table II, below, which were prepared by mixing different proportions of PBST (phosphate buffered saline containing 0.01% Tween 80) and 10 mM arginine-HCl, pH 7.4. The samples were then concentrated over 10-fold, diluted with 2 ml of the same buffer and concentrated again. The dilution and concentration steps were then repeated 2 additional times. The concentration of t-PA in the final concentrate was measured by High Performance Liquid Chromatographic (HPLC) gel filtration of 10 μl samples, integration of the absorbance at 280 nm, and comparison with the 280 nm absorbance obtained from 10 μl (11 μg) of the original untreated melanoma t-PA (ADI Lot 52-03). A DuPont GF 250 HPLC column (9.4 mm×25 cm) and an elution buffer consisting of 1.6M KSCN, 20 mM sodium phosphate, pH 6.8, and 0.01% Tween 80 were used for the HPLC gel filtration step. Table II, below, sets forth the results of these tests. The results show that, with constant ionic strength, increases in the amount of arginine in the aqueous solution of t-PA provide corresponding increases in the solubility of the t-PA. A comparison was made with 1M $NH_4HCO_3$ which is a known protein solubilizer but would be detrimental to the patient's blood gas level and ammonia balance.

TABLE II

| Buffer used | Final concentrate t-PA concentration (mg/ml) | volume (μl) | recovery (%) |
| --- | --- | --- | --- |
| PBST | 0.17 | 72 | 11 |
| PBST: 150 mM Arg—HCl: | | | |
| (99:1) (1.5 mM Arg) | 0.28 | 65 | 16 |
| (90:10) (15 mM Arg) | 0.47 | 51 | 22 |
| (50:50) (75 mM Arg) | 0.60 | 42 | 23 |
| 150 mM Arg—HCl | 2.21 | 38 | 76 |
| 1 M $NH_4HCO_3$ | 3.10 | 30 | 85 |

EXAMPLE 3

This example illustrates the solubility and recovery of melanoma t-PA dialyzed and concentrated in the presence of PBSAT (phosphate buffered saline containing 0.01% $NaN_3$ and 0.01% Tween 80), 0.15M arginine-HCl, pH 7.4, 0.15M lysine-HCl, pH 7.4, and 0.15M ornithine-HCl, pH 7.4. About 120,000 IU of melanoma t-PA (30% single-chain, 70% two-chain, same Product and Lot numbers as in Example 1) in 6 ml of PBSAT was dialyzed against each of the above solutions and then concentrated about 70-fold to a volume of 85 μl. Activity of t-PA was measured before and after this concentration step. Table III, below, sets forth the results of these tests. The results show the relative solubilizing effects of the three named positively charged amino acids. Both arginine and lysine provide substantially greater solubility than ornithine while arginine is somewhat better than lysine in these tests.

TABLE III

| t-PA Solvent | After dialysis, before concentration Activity (IU/ml) | Vol. (ml) | Total Activity (IU) | After dialysis and concentration Activity (IU/ml) | Vol. (μl) | Total Activity (IU) | Recovery (%) |
| --- | --- | --- | --- | --- | --- | --- | --- |
| PBSAT | 20,300 | 6.1 | 124,000 | 158,000 | 85 | 13,400 | 11 |
| Arg | 24,400 | 5.6 | 137,000 | 1,190,000 | 85 | 101,200 | 74 |
| Lys | 24,700 | 5.6 | 138,000 | 1,120,000 | 85 | 95,200 | 69 |
| Orn | 25,800 | 5.7 | 147,000 | 867,000 | 85 | 73,700 | 50 |

EXAMPLE 4

This example illustrates the effect of arginine, lysine and ornithine on the activity of t-PA in aqueous solution in the parabolic rate assay. These amino acids were expected to inhibit the assay due to inhibition of the binding of t-PA to fibrin and, thereby, inhibit stimulation in the assay by the fibrinogen fragment stimulator used. However, it was unexpectedly found that arginine was significantly less inhibitory than either lysine or ornithine. The results of these tests are shown in the accompanying FIGURE. The samples were assayed in duplicate as indicated by the duplicate points for each amino acid at each concentration level indicated in the FIGURE. The results indicate that treatment of the t-PA solution with 1.5 mM arginine does not significantly inhibit the fibrinolytic activity of the t-PA whereas similar concentrations of lysine or ornithine substantially inhibit the t-PA activity. The results means that one could administer a variety of formulations of the arginine-containing t-PA solution without inhibiting the t-PA activity, for example, 7.5 ml of 1M arginine or 50 ml of 0.15M arginine, provided that upon dilution in the patient's blood (assuming a patient level of 5 liters of blood) the arginine level does not exceed about 1.5 mM concentration.

Various other examples will be apparent to the person skilled in the art after reading the present disclosure without departing from the spirit and scope of the invention. It is intended that all such other examples be included within the scope of the appended claims.

What is claimed is:

1. The method of enhancing the solubility of tissue plasminogen activator in aqueous physiological saline solution comprising incorporating in said solution about 0.01% Tween 80 and a non-toxic salt of arginine in an amount effective to increase the solubility of the t-PA without substantially inhibiting its potential biological activity upon administration.

* * * * *